(12) United States Patent
Stopek (née Prommersberger) et al.

(10) Patent No.: US 9,636,850 B2
(45) Date of Patent: May 2, 2017

(54) BUTTRESS AND SURGICAL STAPLING APPARATUS

(71) Applicant: COVIDIEN LP, Mansfield, MA (US)

(72) Inventors: Megan Stopek (née Prommersberger), St. Louis Park, MN (US); Brian Nentwick, Greenfield Center, NY (US); Philippe Gravagna, Irigny (FR); Yves Bayon, Lyons (FR); Dagmar Dassonville, Charnoz (FR); Alfredo Meneghin, Laval (FR); Julie Lecuivre, Le Bois d'Oingt (FR)

(73) Assignee: Covidien LP, Mansfield, MA (US)

( * ) Notice: Subject to any disclaimer, the term of this patent is extended or adjusted under 35 U.S.C. 154(b) by 164 days.

(21) Appl. No.: 14/178,927

(22) Filed: Feb. 12, 2014

(65) Prior Publication Data

US 2014/0158742 A1 Jun. 12, 2014

Related U.S. Application Data

(60) Continuation of application No. 13/945,218, filed on Jul. 18, 2013, now Pat. No. 9,005,243, which is a continuation of application No. 13/274,521, filed on Oct. 17, 2011, now Pat. No. 8,496,683, which is a division of application No. 11/823,340, filed on Jun. 27, 2007, now Pat. No. 8,062,330.

(51) Int. Cl.
*A61B 17/04* (2006.01)
*B29C 39/12* (2006.01)
*A61B 17/072* (2006.01)
*A61B 17/00* (2006.01)

(52) U.S. Cl.
CPC .......... *B29C 39/123* (2013.01); *A61B 17/072* (2013.01); *A61B 17/07207* (2013.01); *A61B 17/07292* (2013.01); *A61B 2017/00526* (2013.01); *A61B 2017/00849* (2013.01); *A61B 2017/00889* (2013.01); *A61B 2017/00893* (2013.01)

(58) Field of Classification Search
CPC ............ A61B 17/07207; A61B 17/072; A61B 17/07292; A61B 17/068; A61B 2017/07214; B29C 39/123
See application file for complete search history.

(56) References Cited

U.S. PATENT DOCUMENTS 3,054,406 A 9/1962 Usher
3,079,606 A 3/1963 Bobrov
3,124,136 A 3/1964 Usher
(Continued)

FOREIGN PATENT DOCUMENTS

CA 2282761 A1 9/1998
CA 2 667 434 5/2008
(Continued)

OTHER PUBLICATIONS

Extended European Search Report corresponding to EP 14 16 9739.1, completed Aug. 19, 2014 and Aug. 29, 2014; (7 pp).
(Continued)

*Primary Examiner* — Gregory Anderson
*Assistant Examiner* — Christina Lauer

(57) ABSTRACT

Multilayer structures including a porous layer and a non-porous layer are useful as buttresses when associated with a surgical stapling apparatus.

23 Claims, 5 Drawing Sheets

(56) References Cited

U.S. PATENT DOCUMENTS

| | | |
|---|---|---|
| 3,490,675 A | 1/1970 | Green |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby |
| 4,655,221 A | 4/1987 | Devereux |
| 4,834,090 A | 5/1989 | Moore |
| 4,838,884 A | 6/1989 | Dumican |
| 4,927,640 A | 5/1990 | Dahlinder |
| 4,930,674 A | 6/1990 | Barak |
| 5,002,551 A | 3/1991 | Linsky |
| 5,014,899 A | 5/1991 | Presty |
| 5,040,715 A | 8/1991 | Green |
| 5,065,929 A | 11/1991 | Schulze |
| 5,112,496 A | 5/1992 | Dhawan et al. |
| 5,205,459 A | 4/1993 | Brinkerhoff |
| 5,263,629 A | 11/1993 | Trumbull |
| 5,281,197 A | 1/1994 | Arias et al. |
| 5,307,976 A | 5/1994 | Olson |
| 5,312,023 A | 5/1994 | Green |
| 5,314,471 A | 5/1994 | Brauker |
| 5,318,221 A | 6/1994 | Green |
| 5,326,013 A | 7/1994 | Green |
| 5,332,142 A | 7/1994 | Robinson |
| 5,344,454 A | 9/1994 | Clarke |
| 5,392,979 A | 2/1995 | Green |
| 5,397,324 A | 3/1995 | Carroll et al. |
| 5,405,072 A | 4/1995 | Zlock et al. |
| 5,425,745 A | 6/1995 | Green |
| 5,441,193 A | 8/1995 | Gravener |
| 5,441,507 A | 8/1995 | Wilk |
| 5,443,198 A | 8/1995 | Viola |
| 5,468,253 A | 11/1995 | Bezwada |
| 5,503,638 A | 4/1996 | Cooper |
| 5,542,594 A | 8/1996 | McKean |
| 5,549,628 A | 8/1996 | Cooper |
| 5,575,803 A | 11/1996 | Cooper |
| 5,653,756 A | 8/1997 | Clarke |
| 5,683,809 A | 11/1997 | Freeman |
| 5,690,675 A | 11/1997 | Sawyer |
| 5,702,409 A | 12/1997 | Rayburn |
| 5,752,965 A | 5/1998 | Francis |
| 5,762,256 A | 6/1998 | Mastri |
| 5,766,188 A | 6/1998 | Igaki |
| 5,769,892 A | 6/1998 | Kingwell |
| 5,782,396 A | 7/1998 | Mastri |
| 5,799,857 A | 9/1998 | Robertson |
| 5,810,855 A | 9/1998 | Rayburn |
| 5,814,057 A | 9/1998 | Oi |
| 5,833,695 A | 11/1998 | Yoon |
| 5,843,096 A | 12/1998 | Igaki |
| 5,871,135 A | 2/1999 | Williamson, IV et al. |
| 5,895,412 A | 4/1999 | Tucker |
| 5,895,415 A | 4/1999 | Chow |
| 5,902,312 A | 5/1999 | Frater et al. |
| 5,908,427 A | 6/1999 | McKean |
| 5,915,616 A | 6/1999 | Viola |
| 5,931,847 A | 8/1999 | Bittner |
| 5,964,394 A | 10/1999 | Robertson |
| 5,964,774 A | 10/1999 | McKean |
| 5,997,895 A | 12/1999 | Narotam |
| 6,019,791 A | 2/2000 | Wood |
| 6,030,392 A | 2/2000 | Dakov |
| 6,032,849 A | 3/2000 | Mastri |
| 6,045,560 A | 4/2000 | McKean |
| 6,063,097 A | 5/2000 | Oi |
| 6,080,169 A | 6/2000 | Turtel |
| 6,099,551 A | 8/2000 | Gabbay |
| 6,149,667 A | 11/2000 | Hovland |
| 6,155,265 A | 12/2000 | Hammerslag |
| 6,210,439 B1 | 4/2001 | Firmin |
| 6,214,020 B1 | 4/2001 | Mulhauser |
| 6,241,139 B1 | 6/2001 | Milliman |
| 6,258,107 B1 | 7/2001 | Balazs |
| 6,267,772 B1 | 7/2001 | Mulhauser |
| 6,273,897 B1 | 8/2001 | Dalessandro |
| 6,280,453 B1 | 8/2001 | Kugel |
| 6,299,631 B1 | 10/2001 | Shalaby |
| 6,312,457 B1 | 11/2001 | DiMatteo |
| 6,312,474 B1 | 11/2001 | Francis |
| 6,325,810 B1 * | 12/2001 | Hamilton ......... A61B 17/07207 227/175.1 |
| 6,330,965 B1 | 12/2001 | Milliman |
| 6,436,030 B2 | 8/2002 | Rehil |
| 6,454,780 B1 | 9/2002 | Wallace |
| 6,461,368 B2 | 10/2002 | Fogarty |
| 6,503,257 B2 | 1/2003 | Grant |
| 6,514,283 B2 | 2/2003 | DiMatteo |
| 6,517,566 B1 | 2/2003 | Hovland |
| 6,551,356 B2 | 4/2003 | Rousseau |
| 6,568,398 B2 | 5/2003 | Cohen |
| 6,592,597 B2 | 7/2003 | Grant |
| 6,596,304 B1 | 7/2003 | Bayon |
| 6,638,285 B2 | 10/2003 | Gabbay |
| 6,652,594 B2 | 11/2003 | Francis |
| 6,656,193 B2 | 12/2003 | Grant |
| 6,669,735 B1 | 12/2003 | Pelissier |
| 6,677,258 B2 | 1/2004 | Carroll |
| 6,685,714 B2 | 2/2004 | Rousseau |
| 6,702,828 B2 | 3/2004 | Whayne |
| 6,704,210 B1 | 3/2004 | Myers |
| 6,706,684 B1 | 3/2004 | Bayon |
| 6,723,114 B2 | 4/2004 | Shalaby |
| 6,726,706 B2 | 4/2004 | Dominguez |
| 6,736,823 B2 | 5/2004 | Darois |
| 6,736,854 B2 | 5/2004 | Vadurro |
| 6,746,458 B1 | 6/2004 | Cloud |
| 6,773,458 B1 | 8/2004 | Brauker |
| 6,896,684 B2 | 5/2005 | Monassevitch |
| 6,927,315 B1 | 8/2005 | Heinecke |
| 6,939,358 B2 | 9/2005 | Palacios |
| 6,946,196 B2 | 9/2005 | Foss |
| 6,959,851 B2 | 11/2005 | Heinrich |
| 7,060,087 B2 | 6/2006 | DiMatteo |
| 7,087,065 B2 | 8/2006 | Ulmsten |
| 7,108,701 B2 | 9/2006 | Evens |
| 7,128,253 B2 | 10/2006 | Mastri |
| 7,128,748 B2 | 10/2006 | Mooradian |
| 7,134,438 B2 | 11/2006 | Makower et al. |
| 7,141,055 B2 | 11/2006 | Abrams |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et |
| 7,232,449 B2 | 6/2007 | Sharkawy |
| 7,241,300 B2 | 7/2007 | Sharkawy |
| 7,307,031 B2 | 12/2007 | Carroll |
| 7,311,720 B2 | 12/2007 | Mueller |
| 7,368,124 B2 | 5/2008 | Chun |
| 7,377,928 B2 | 5/2008 | Zubik |
| 7,434,717 B2 | 10/2008 | Shelton, IV |
| 7,438,209 B1 | 10/2008 | Hess |
| 7,547,312 B2 | 6/2009 | Bauman et al. |
| 7,559,937 B2 | 7/2009 | de la Torre |
| 7,571,845 B2 | 8/2009 | Viola |
| 7,594,921 B2 | 9/2009 | Browning |
| 7,604,151 B2 | 10/2009 | Hess |
| 7,665,646 B2 | 2/2010 | Prommersberger |
| 7,666,198 B2 | 2/2010 | Suyker |
| 7,669,747 B2 | 3/2010 | Weisenburgh, II |
| 7,717,313 B2 | 5/2010 | Bettuchi |
| 7,722,642 B2 | 5/2010 | Williamson, IV |
| 7,744,627 B2 | 6/2010 | Orban, III |
| 7,776,060 B2 | 8/2010 | Mooradian |
| 7,793,813 B2 | 9/2010 | Bettuchi |
| 7,799,026 B2 | 9/2010 | Schechter |
| 7,823,592 B2 | 11/2010 | Bettuchi |
| 7,824,420 B2 | 11/2010 | Eldridge |
| 7,845,533 B2 | 12/2010 | Marczyk |
| 7,845,536 B2 | 12/2010 | Viola |
| 7,846,149 B2 | 12/2010 | Jankowski |
| 7,892,247 B2 | 2/2011 | Conston |

(56) References Cited

U.S. PATENT DOCUMENTS

| | | |
|---|---|---|
| 7,909,224 B2 | 3/2011 | Prommersberger |
| 7,909,837 B2 | 3/2011 | Crews |
| 7,938,307 B2 | 5/2011 | Bettuchi |
| 7,942,890 B2 | 5/2011 | D'Agostino |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,011,555 B2 | 9/2011 | Tarinelli |
| 8,016,177 B2 | 9/2011 | Bettuchi |
| 8,016,178 B2 | 9/2011 | Olson |
| 8,028,883 B2 | 10/2011 | Stopek |
| 8,038,045 B2 | 10/2011 | Bettuchi |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,127,975 B2 | 3/2012 | Olson et al. |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino et al. |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi |
| 8,366,787 B2 | 2/2013 | Brown |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull |
| 8,474,677 B2 | 7/2013 | Woodard, Jr. |
| 8,479,968 B2 | 7/2013 | Hodgkinson |
| 8,485,414 B2 | 7/2013 | Criscuolo |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 9,433,412 B2 | 9/2016 | Bettuchi et al. |
| 9,433,413 B2 | 9/2016 | Stopek |
| 2002/0028243 A1 | 3/2002 | Masters |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1* | 11/2002 | Grant ............... A61B 17/072 606/151 |
| 2003/0007955 A1* | 1/2003 | Rees ............... A61K 38/1808 424/93.21 |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian |
| 2003/0196668 A1 | 10/2003 | Harrison et al. |
| 2003/0208231 A1 | 11/2003 | Williamson, IV |
| 2004/0107006 A1 | 6/2004 | Francis |
| 2004/0132365 A1 | 7/2004 | Therin |
| 2004/0175408 A1* | 9/2004 | Chun ............... A61F 2/08 424/426 |
| 2004/0254590 A1 | 12/2004 | Hoffman |
| 2004/0260315 A1 | 12/2004 | Dell |
| 2005/0002981 A1 | 1/2005 | Lahtinen |
| 2005/0021085 A1 | 1/2005 | Abrams |
| 2005/0059996 A1 | 3/2005 | Bauman |
| 2005/0059997 A1* | 3/2005 | Bauman ............... A61B 17/072 606/219 |
| 2005/0070929 A1 | 3/2005 | Dalessandro |
| 2005/0118435 A1 | 6/2005 | DeLucia |

(56) References Cited

U.S. PATENT DOCUMENTS

| | | |
|---|---|---|
| 2005/0149073 A1 | 7/2005 | Arani |
| 2005/0228446 A1 | 10/2005 | Mooradian et al. |
| 2006/0004407 A1 | 1/2006 | Hiles |
| 2006/0085030 A1 | 4/2006 | Bettuchi et al. |
| 2006/0135992 A1 | 6/2006 | Bettuchi |
| 2006/0173470 A1 | 8/2006 | Oray |
| 2006/0178683 A1 | 8/2006 | Shimoji |
| 2006/0271104 A1 | 11/2006 | Viola |
| 2007/0026031 A1 | 2/2007 | Bauman |
| 2007/0034669 A1 | 2/2007 | de la Torre |
| 2007/0049953 A2 | 3/2007 | Shimoji |
| 2007/0123839 A1 | 5/2007 | Rousseau |
| 2007/0179528 A1 | 8/2007 | Soltz |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia |
| 2008/0009811 A1 | 1/2008 | Cantor |
| 2008/0029570 A1 | 2/2008 | Shelton |
| 2008/0082126 A1 | 4/2008 | Murray |
| 2008/0110959 A1 | 5/2008 | Orban |
| 2008/0125812 A1 | 5/2008 | Zubik |
| 2008/0140115 A1 | 6/2008 | Stopek |
| 2008/0161831 A1 | 7/2008 | Bauman |
| 2008/0161832 A1 | 7/2008 | Bauman |
| 2008/0169327 A1 | 7/2008 | Shelton |
| 2008/0169328 A1 | 7/2008 | Shelton |
| 2008/0169329 A1 | 7/2008 | Shelton |
| 2008/0169330 A1 | 7/2008 | Shelton |
| 2008/0169331 A1 | 7/2008 | Shelton |
| 2008/0169332 A1 | 7/2008 | Shelton |
| 2008/0169333 A1 | 7/2008 | Shelton |
| 2008/0200949 A1 | 8/2008 | Hiles |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi |
| 2008/0308608 A1 | 12/2008 | Prommersberger |
| 2008/0314960 A1 | 12/2008 | Marczyk |
| 2009/0001121 A1 | 1/2009 | Hess |
| 2009/0001122 A1 | 1/2009 | Prommersberger |
| 2009/0001123 A1 | 1/2009 | Morgan |
| 2009/0001124 A1 | 1/2009 | Hess |
| 2009/0001125 A1 | 1/2009 | Hess |
| 2009/0001126 A1 | 1/2009 | Hess |
| 2009/0001128 A1 | 1/2009 | Weisenburgh, II |
| 2009/0001130 A1 | 1/2009 | Hess |
| 2009/0005808 A1 | 1/2009 | Hess |
| 2009/0030452 A1 | 1/2009 | Bauman |
| 2009/0043334 A1 | 2/2009 | Bauman |
| 2009/0076510 A1 | 3/2009 | Bell |
| 2009/0076528 A1 | 3/2009 | Sgro |
| 2009/0078739 A1 | 3/2009 | Viola |
| 2009/0095791 A1 | 4/2009 | Eskaros |
| 2009/0095792 A1 | 4/2009 | Bettuchi |
| 2009/0120994 A1 | 5/2009 | Murray |
| 2009/0134200 A1 | 5/2009 | Tarinelli |
| 2009/0206125 A1 | 8/2009 | Huitema |
| 2009/0206126 A1 | 8/2009 | Huitema |
| 2009/0206139 A1 | 8/2009 | Hall |
| 2009/0206141 A1 | 8/2009 | Huitema |
| 2009/0206142 A1 | 8/2009 | Huitema |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino |
| 2010/0012704 A1 | 1/2010 | Tarinelli Racenet |
| 2010/0065606 A1 | 3/2010 | Stopek |
| 2010/0065607 A1 | 3/2010 | Orban, III |
| 2010/0072254 A1 | 3/2010 | Aranyi |
| 2010/0147921 A1 | 6/2010 | Olson |
| 2010/0147922 A1 | 6/2010 | Olson |
| 2010/0147923 A1 | 6/2010 | D'Agostino |
| 2010/0243707 A1 | 9/2010 | Olson |
| 2010/0243708 A1 | 9/2010 | Aranyi |
| 2010/0243711 A1 | 9/2010 | Olson |
| 2010/0249805 A1 | 9/2010 | Olson |
| 2010/0264195 A1 | 10/2010 | Bettuchi |
| 2010/0282815 A1 | 11/2010 | Bettuchi |
| 2010/0331880 A1 | 12/2010 | Stopek |
| 2011/0024476 A1 | 2/2011 | Bettuchi |
| 2011/0024481 A1 | 2/2011 | Bettuchi |
| 2011/0036894 A1 | 2/2011 | Bettuchi |
| 2011/0042442 A1 | 2/2011 | Viola |
| 2011/0046650 A1 | 2/2011 | Bettuchi |
| 2011/0057016 A1 | 3/2011 | Bettuchi |
| 2011/0087279 A1 | 4/2011 | Shah |
| 2011/0215132 A1 | 9/2011 | Aranyi |
| 2012/0074199 A1 | 3/2012 | Olson |
| 2012/0080336 A1 | 4/2012 | Shelton |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson |
| 2013/0037596 A1 | 2/2013 | Bear |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |

(56) References Cited

U.S. PATENT DOCUMENTS

| | | |
|---|---|---|
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| CN | 101310680 A | 11/2008 |
| CN | 101332110 A | 12/2008 |
| DE | 1 99 24 311 | 11/2000 |
| EP | 0 594 148 | 4/1994 |
| EP | 0 327 022 | 4/1995 |
| EP | 0 667 119 | 8/1995 |
| EP | 1 064 883 | 1/2001 |
| EP | 1 256 317 | 11/2002 |
| EP | 1 256 318 | 11/2002 |
| EP | 1 520 525 | 4/2005 |
| EP | 1 621 141 | 2/2006 |
| EP | 1 702 570 | 9/2006 |
| EP | 1 759 640 | 3/2007 |
| EP | 1 815 804 | 8/2007 |
| EP | 1 825 820 | 8/2007 |
| EP | 1 929 958 | 6/2008 |
| EP | 1 994 890 | 11/2008 |
| EP | 2 005 894 | 12/2008 |
| EP | 2 005 895 | 12/2008 |
| EP | 2 008 595 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 | 6/2010 |
| EP | 2 236 098 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 2007-124166 | 5/2007 |
| WO | WO 90/05489 | 5/1990 |
| WO | WO 95/16221 | 6/1995 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | 98/38923 A1 | 9/1998 |
| WO | WO 99/45849 | 9/1999 |
| WO | WO 03/082126 | 10/2003 |
| WO | WO 03/088845 | 10/2003 |
| WO | WO 03/094743 | 11/2003 |
| WO | WO 03/105698 | 12/2003 |
| WO | WO 2005/079675 | 9/2005 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 | 7/2010 |
| WO | WO 2011/143183 | 11/2011 |
| WO | WO 2012/044848 | 4/2012 |

OTHER PUBLICATIONS

Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
European Search Report corresponding to EP 05 02 2585.3, completed Jan. 25, 2006 and mailed Feb. 3, 2006; (4 pp).
European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).
European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).

(56) References Cited

OTHER PUBLICATIONS

European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 20131; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 13 19 2123.1, completed Jan. 30, 2014 and mailed Feb. 10, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).
Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Intl Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.

(56) References Cited

OTHER PUBLICATIONS

European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 mailed Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 mailed Jul. 26, 2016.
Japanese Office Action corresponding to counterpart Int'l Appln. No. JP 2012-268668 mailed Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 mailed Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 mailed Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 mailed Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.

* cited by examiner

BUTTRESS AND SURGICAL STAPLING APPARATUS

CROSS-REFERENCE TO RELATED APPLICATIONS

This application is a Continuation of U.S. patent application Ser. No. 13/945,218, filed Jul. 18, 2013, which is a Continuation of U.S. patent application Ser. No. 13/274,521, filed Oct. 17, 2011, now U.S. Pat. No. 8,496,683, which is a Divisional of U.S. patent application Ser. No. 11/823,340 filed Jun. 27, 2007, now U.S. Pat. No. 8,062,330, the entire disclosures of each of the above-identified applications being hereby incorporated by reference.

BACKGROUND

Technical Field

The present disclosure relates to surgical buttresses which can be releasably attached to a surgical stapling apparatus. The buttresses contain a porous layer and a non-porous layer.

Background of Related Art

Surgical stapling devices have found widespread application in surgical operations where body tissue must be joined or removed. When operating on certain tissue, such as lung, esophageal, intestinal, duodenal, and vascular tissue, it is important to effectively seal the tissue which can be particularly prone to air or fluid leakage. Preventing or reducing air or fluid leakage can significantly decrease post operative recovery time. Thus, it would be advantageous to provide a material for use with a surgical stapling device which enhances sealing at the surgical wound site.

SUMMARY

Buttresses having a porous layer and a non-porous layer are described herein. The multilayer buttresses are suitable for use in connection with a surgical stapling apparatus and assist in the sealing of tissue to prevent the leakage of fluids and gases. The surgical stapling apparatus includes a staple cartridge having a surface with at least one opening through which a staple may be ejected. The surgical stapling apparatus further includes an anvil having a surface against which an ejected staple may be deformed. A buttress in accordance with the present disclosure may be associated with either the staple cartridge, the anvil, or both.

In embodiments, the porous layer possesses haemostatic properties. In embodiments, the non-porous layer has anti-adhesion properties.

DETAILED DESCRIPTION OF PREFERRED EMBODIMENTS

Figure 1:
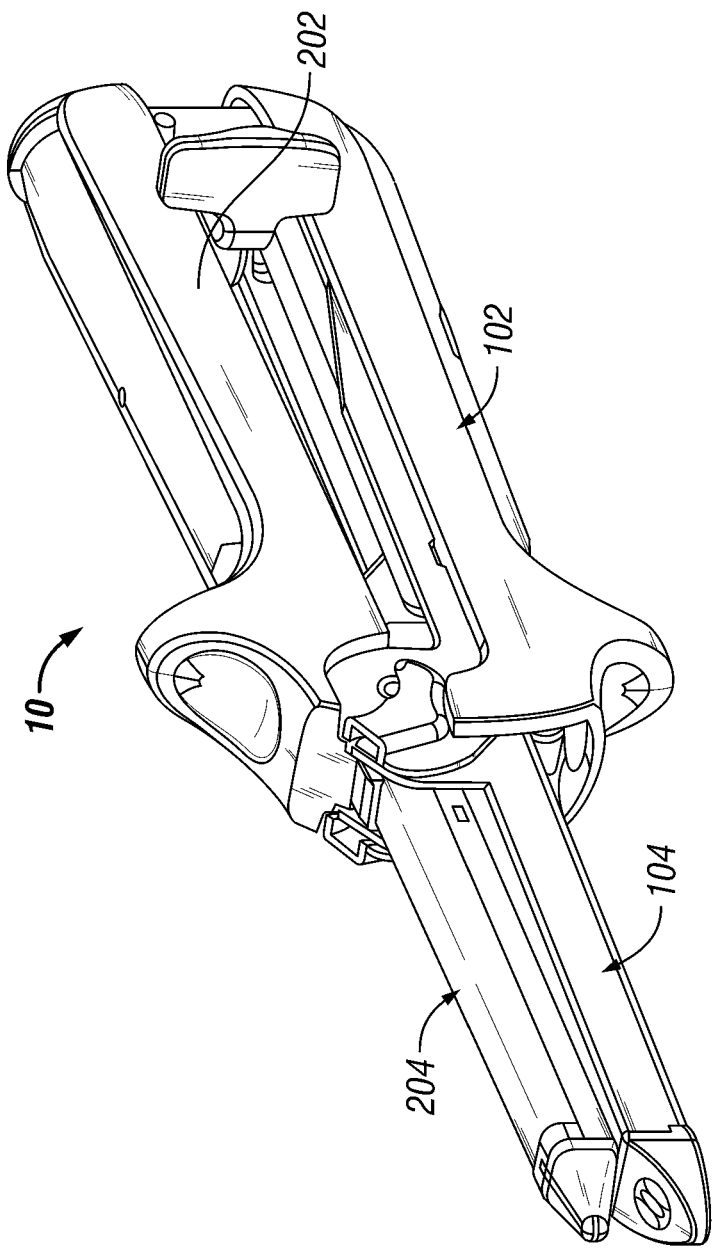
FIG. 1 is a perspective view of one illustrative embodiment of a linear surgical stapling apparatus.
Figure 2A:
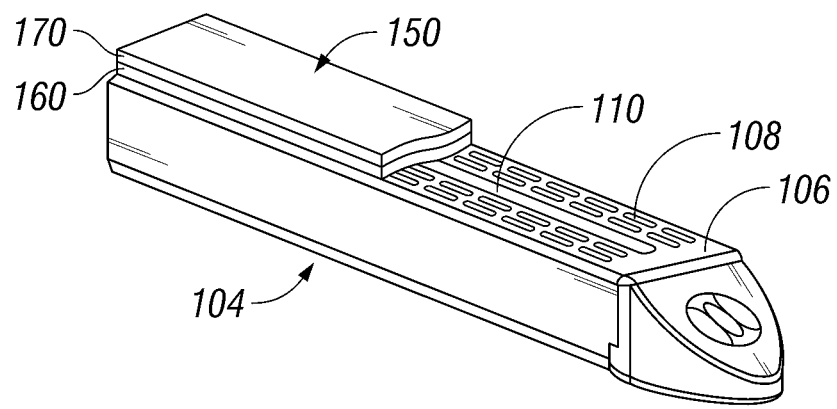
FIG. 2A is a perspective view of a staple cartridge that includes a multilayer buttress in accordance with the present disclosure.
Figure 2B:
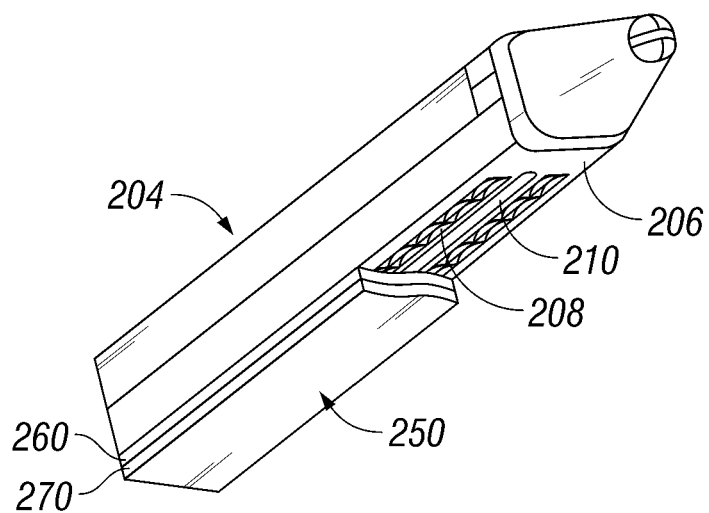
FIG. 2B is a perspective view of a staple anvil that includes a multilayer buttress in accordance with the present disclosure.

Embodiments of the presently disclosed multilayer buttress and surgical stapling apparatus will now be described in detail with reference to the drawing figures wherein like reference numerals identify similar or identical elements.

The multilayer surgical buttress described herein may be used in sealing a wound by approximating the edges of wound tissue between the staple cartridge and the staple anvil of a stapling apparatus which contains at least one multilayer surgical buttress having a non-porous layer and a porous layer and firing the stapling apparatus to force at least one staple to pass through the openings on the staple cartridge, at least one multilayer buttress, the tissue and the openings on the staple anvil to seal the tissue. Once stapled in place the porous layer advantageously reduces bleeding, assists in sealing the wound and allowing tissue ingrowth, if desired, while the non-porous layer provides support for the porous layer and may assist in preventing the formation of adhesions.

In addition, the multilayer buttress may optionally include an additional reinforcement member (which, as described in more detailed below, may be absorbable or non-absorbable) to provide additional support to the multilayer buttress and assist in preventing tears during stapling.

It should be understood that buttresses need not be associated with both the staple cartridge and the anvil. Rather, a buttress may be associated with only the staple cartridge and not the anvil or with the anvil and not the staple cartridge. In addition, the multilayer surgical buttress described herein may be configured into any shape, size or dimension suitable to fit any surgical stapling, fastening or firing apparatus. Other examples of stapling apparatus which may utilize the multilayer buttress material described herein includes laparoscopic staplers (see, e.g., U.S. Pat. Nos. 6,330,965 and 6,241,139, the entire contents of which are incorporated herein by this reference), alternative stapling apparatus of the transverse anastomosis type for stapling a patient's mesentery (see, e.g., U.S. Pat. No. 5,964,394, the entire content of which is incorporated herein by this reference), and end-to-end anastomosis types for performing surgical anastomotic stapling with a circular cartridge and anvil mesentery (see, e.g., U.S. Pat. No. 5,915,616, the entire content of which is incorporated herein by this reference). The present buttresses may also be used in conjunction with instruments that apply two-part fasteners wherein a first part of the two-part fastener is stored in a cartridge or like member and can be fired and properly joined to a second part of the two-part fastener disposed in an anvil or like member. Those skilled in the art having read the present disclosure will readily envision how to adapt the present buttresses for use in connection with such apparatus and also envision other surgical apparatus with which the buttresses described herein may be used.

Figure 3A:
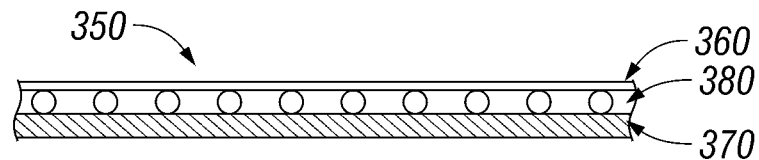
FIG. 3A is a side view of a multilayer buttress as described in one embodiment herein.
Figure 3B:
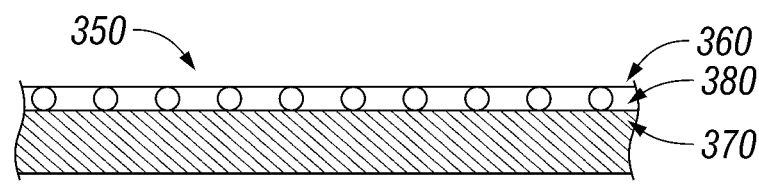
FIG. 3B is a side view of a multilayer buttress as described in one embodiment herein.

Now turning to FIGS. 3A and 3B, buttress 350 is shown having a non-porous layer 360 and a porous layer 370. It is envisioned that buttress 350 may contain a plurality of layers in which any combination of non-porous and porous layers may be configured. For example, a multilayer buttress may be formed in which multiple non-porous layers and porous layers are stacked in an alternating manner. In another example, the multilayer buttress may be formed in a "sandwich-like" manner wherein the outer layers of the multilayer buttress include porous layers and the inner layers are non-porous layers. It is further envisioned that the non-porous layer and porous layer may be positioned in any order relative to the surfaces of staple cartridge and staple anvil.

The non-porous layer of the buttress may be made from any biocompatible material. Thus, the non-porous layer of the multilayer buttress described herein may be formed from a natural material or a synthetic material. The material from which the non-porous layer is formed may be bioabsorbable or non-bioabsorbable. It should of course be understood that any combination of natural, synthetic, bioabsorbable and non-bioabsorbable materials may be used to form the non-porous layer. Some non-limiting examples of materials from which the non-porous layer may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the non-porous layer of the buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce the support layer of the buttress.

In embodiments, collagen of human and/or animal origin, e.g., type I porcine or bovine collagen, type I human collagen or type III human collagen, may be used to form the non-porous layer.

Native collagen may advantageously be used in acid solution or after processing, to eliminate the telopetpides, notably by pepsin digestion. The collagen, e.g., atelocollagen, can also be modified by oxidative cleavage by the use of periodic acid or one of its salts. The oxidative cleavage of the collagen allows for future moderate crosslinking in the collagenic material with other polymeric materials, macromolecular additives or the haemostatic agents contained in the haemostatic layer of the buttress.

In embodiments, the non-porous layer according to the present disclosure is made of collagen which is oxidized or a mixture in any proportions of non-oxidized and oxidized collagens.

In embodiments, at least one macromolecular additive may be combined with the collagen to provide a composition from which the non-porous layer is formed. Some examples of suitable macromolecular additives include, polyethylene glycol, glycerin, polysaccharides, dextran, maltodextrin, mucopolysaccharides, cellulose, alginate and combinations thereof. When used, the macromolecular additive may have a molecular weight of at least 3,000 Daltons and may represent a concentration from about 2 to 10 times less than the collagenic material present in the composition from which the non-porous layer is formed.

The non-porous layer may enhance the ability of the buttress to resist tears and perforations during the manufacturing, shipping, handling and stapling processes. Also, the non-porous layer may also retard or prevent tissue ingrowth from surrounding tissues thereby acting as an adhesion barrier and preventing the formation of unwanted scar tissue. Thus, in embodiments, the non-porous layer possesses anti-adhesion properties.

It is envisioned that the buttress may be releasably attached to the cartridge and/or the anvil in any manner capable of retaining the buttress in contact with the cartridge and/or the anvil prior to and during the stapling process, while allowing the buttress to be removed or released from the cartridge and/or the anvil following the penetration of the buttress by a surgical staple or other fastening device. For example, the buttress may be attached to the cartridge and/or the anvil using adhesives, sealants, glues, pins, tacks, tabs, clamps, channels, straps, protrusions and combinations thereof.

The non-porous layer may be formed using techniques within the purview of those skilled in the art, such as casting, molding and the like.

Figure 5A:
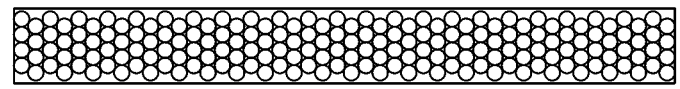
FIG. 5A schematically shows a porous layer wherein the pores or openings extend across the entire thickness thereof in accordance with embodiments of the present disclosure.
Figure 5B:
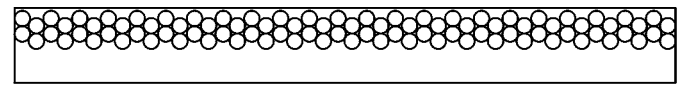
FIG. 5B schematically shows a porous layer wherein the pores or openings do not extend across the entire thickness thereof in accordance with embodiments of the present disclosure.
Figure 5C:
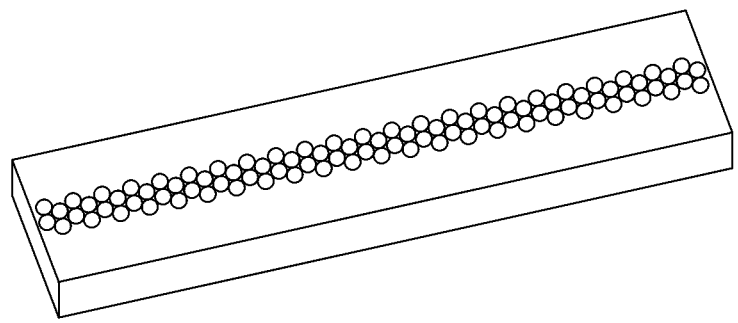
FIG. 5C schematically shows a porous layer wherein the pores or openings are present on only a portion of the surface thereof in accordance with embodiments of the present disclosure.

The porous layer of the buttress has openings or pores over at least a portion of a surface thereof. As described in more detail below, suitable materials for forming the porous layer include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, kitted fabrics and open cell foam are illustrative examples of structures in which the pores can be in sufficient number and size so as to interconnect across the entire thickness of the porous layer. In embodiments, the pores do not interconnect across the entire thickness of the porous layer. Closed cell foam or fused non-woven materials are illustrative examples of structures in which the pores may not interconnect across the entire thickness of the porous layer. FIG. 5A schematically illustrates a foam porous layer wherein the pores span across the entire thickness of porous layer. In yet other embodiments, the pores do not extend across the entire thickness of the porous layer, but rather are present at a portion of the surface thereof. FIG. 5B schematically illustrates a porous layer wherein the pores do not span across the entire thickness thereof. In embodiments, the openings or pores are located on a portion of the surface of the porous layer, with other portions of the porous layer having a non-porous texture. FIG. 5C schematically illustrates a porous layer wherein the pores do not cover the entire surface of the porous layer, but rather are present on a central portion thereof. Those skilled in the art reading the present disclosure will envision other pore distribution patterns and configurations for the porous layer.

Where the porous layer is fibrous, the fibers may be filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers. Some non-limiting examples of materials from which the fibers may be made include, but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

Where the porous layer is fibrous, the porous layer may be formed using any method suitable to forming fibrous structures, including but not limited to knitting, weaving, non-woven techniques and the like. Suitable techniques for making fibrous structures are within the purview of those skilled in the art.

Where the porous layer is a foam, the porous layer may be formed using any method suitable to forming a foam or sponge including, but not limited to the lyophilization or freeze-drying of a composition. Suitable techniques for making foams are within the purview of those skilled in the art.

In embodiments, the porous layer possesses haemostatic properties. Illustrative examples of materials which may be used in providing the porous layer with the capacity to assist in stopping bleeding or hemorrhage include, but are not limited to, poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof.

Generally, the use of natural biological polymers, and in particular proteins, is particularly useful in forming porous layers having haemostatic properties. Suitable natural biological polymers include, but are not limited to, collagen, gelatin, fibrin, fibrinogen, elastin, keratin, albumin and combinations thereof. In such embodiments, the natural biological polymers may be combined with any other haemostatic agent to produce the porous layer of the buttress. The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, the porous layer may be made from denatured collagen or collagen which has at least partially lost its helical structure through heating or any other method, consisting mainly of non-hydrated α chains, of molecular weight close to 100 kDa. The term "denatured collagen" means collagen which has lost its helical structure. The collagen used for the porous layer as described herein may be native collagen or atellocollagen, notably as obtained through pepsin digestion and/or after moderate heating as defined previously. The collagen may have been previously chemically modified by oxidation, methylation, succinylation, ethylation or any other known process.

In embodiments, the porous layer can be obtained by freeze-drying an aqueous acid solution or suspension of collagen at a concentration of about 2 to about 50 g/l and at an initial temperature of about 4 to about 25° C. The concentration of collagen in the solution can be from about 1 g/l to about 30 g/l and in embodiments about 10 g/l. This solution is advantageously neutralized to a pH of about 6 to about 8.

In embodiments, the porous layer can be at least 0.1 cm thick. In embodiments the thickness of the porous layer can range from about 0.2 to about 1.5 cm thick. The porous layer can have a density of not more than about 75 mg collagen/$cm^2$ and in embodiments below about 7 mg collagen/$cm^2$. The size of the pores in the porous layer can be from about 20 μm to about 200 μm, in embodiments from about 100 μm to about 200 μm.

The haemostatic agents from which the porous layer can be made or which can be included in the porous layer can be in the form of foams, fibers, filaments, meshes, woven and non-woven webs, compresses, pads, powders, flakes, particles and combinations thereof. In embodiments, the porous layer having haemostatic properties provides to the multilayer buttress when hydrated characteristics similar to that of the tissue to which the buttress is applied.

The multilayer buttress material described herein may be formed using any method known to those skilled in the art capable of connecting a non-porous layer to a porous layer. It is envisioned that the non-porous layer and the porous layer may be adhered to one another using chemical bonding, surgical adhesives, surgical sealants, and surgical glues. In addition, the layers may be bound together using mechanic means such as pins, rods, screws, clips, etc. Still further, the layers may naturally or through chemical or photoinitiation may interact and crosslink or provide covalent bonding between the layers.

In embodiments, the multilayer buttress described herein is prepared by attaching the individual layers of materials together to form a multiple layer buttress. The porous layer may be formed separate and apart from the non-porous layer. Alternatively, the porous and non-porous layers may be formed together.

In some embodiments, the porous layer may be attached to the non-porous layer, in a manner which allows the two layers to crosslink and form a chemical bond creating a multilayer buttress material capable of sealing tissue. One such example includes pouring a solution of the material from which the non-porous layer is to be made into a mold and applying the porous layer to the poured solution during the gelification process. As described in U.S. Pat. No. 6,596,304, which the entire content of which is incorporated herein by reference, the porous layer may contain a porous compress made from collagen. The non-porous layer may be made from a biopolymer film containing collagen, polyethylene and glycerol. The porous layer may be added to the non-porous film and allowed to crosslink to form multilayer material suitable for reinforcing a staple or suture line.

As further shown in FIGS. 3A and 3B, buttress 350 may also include a reinforcement member 380. In FIG. 3A, reinforcement member 380 is shown being positioned between non-porous layer 360 and porous layer 370 of buttress 350 and in FIG. 3B, reinforcement member 380 is shown being positioned solely within an individual layer, supporting in this case non-porous layer 360 of buttress 350. It is envisioned that reinforcement member 380 may also be positioned within the porous layer. The reinforcement member may also be positioned at the surface of one of the layers making up the multilayer buttress and, in embodiments, may be positioned at an exterior surface of the multilayer buttress.

Figure 3C:
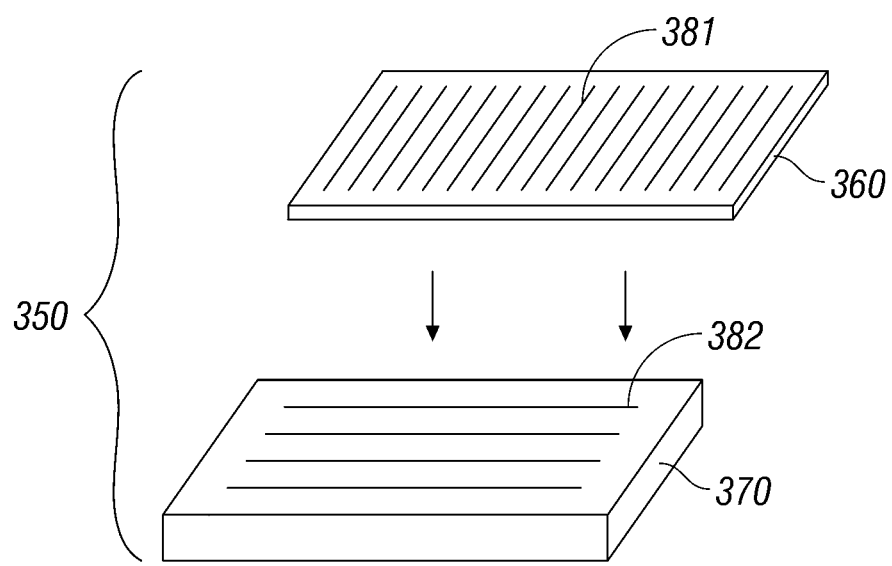
FIG. 3C shows an illustrative embodiment wherein fibers present in more than one layer are used as the reinforcement member, with the fibers in one layer being oriented in a first common direction and the fibers in the other layer being oriented in a second common direction that is substantially perpendicular to the first common direction.
Figure 3D:
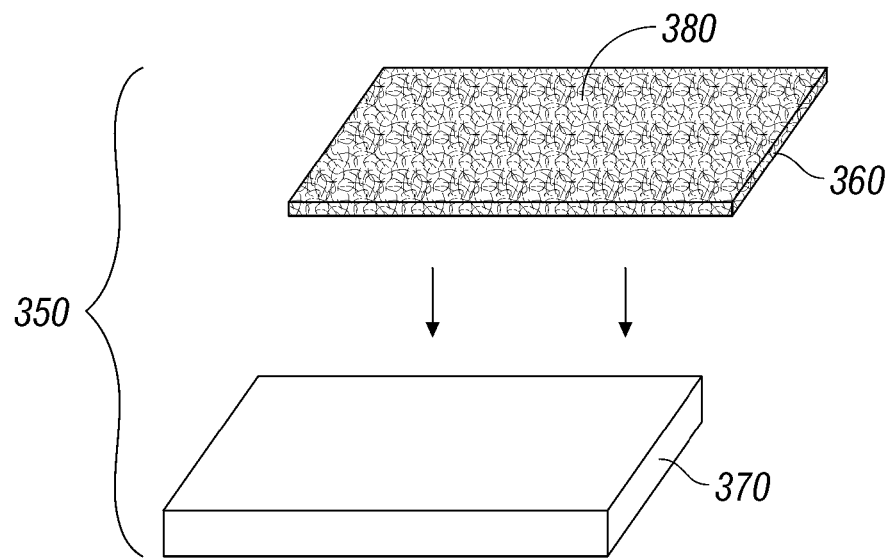
FIG. 3D shows an illustrative embodiment wherein chopped fibers are used as the reinforcement member.

Some suitable non-limiting examples of the reinforcement member include meshes, monofilaments, multifilament braids, chopped fibers (sometimes referred to in the art as staple fibers) and combinations thereof.

Where the reinforcement member is a mesh, it may be prepared using any technique known to those skilled in the art, such as knitting, weaving, tatting, knipling or the like.

Where monofilaments or multifilament braids are used as the reinforcement member, the monofilaments or multifilament braids may be oriented in any desired manner. For example, the monofilaments or multifilament braids may be randomly positioned with respect to each other within the buttress structure. As another example, the monofilaments or multifilament braids may be oriented in a common direction within the buttress. In embodiments, monofilaments or multifilament braids are associated with both the porous layer and with the non-porous layer. In an illustrative embodiment of this type shown in FIG. 3C, buttress 350 includes a first reinforcement member 381 having a plurality of reinforcement members oriented in a first direction within the non-porous layer 360 and a second reinforcement layer 382 having a plurality of reinforcement members oriented in a second direction within the porous layer 370. In embodiments, the first and second directions may be substantially perpendicular to each other as seen in FIG. 3C.

Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. FIG. 3D shows an illustrative embodiment wherein buttress 350 has chopped fibers 380 incorporated in non-porous layer 360 which can be applied to porous layer 370.

It is envisioned that the reinforcement member may be formed from any bioabsorbable, non-bioabsorbable, natural, and synthetic material previously described herein including derivatives, salts and combinations thereof. In particularly useful embodiments, the reinforcement member may be made from a non-bioabsorbable material to provide long term flexible tissue support. In embodiments, the reinforcement member is a surgical mesh made from polypropylene or polylactic acid. In addition polyethylene materials may also be incorporated into the buttress described herein to add stiffness. Where monofilaments or multifilament braids are used as the reinforcement member, any commercially available suture material may advantageously be employed as the reinforcement member.

Figure 4:
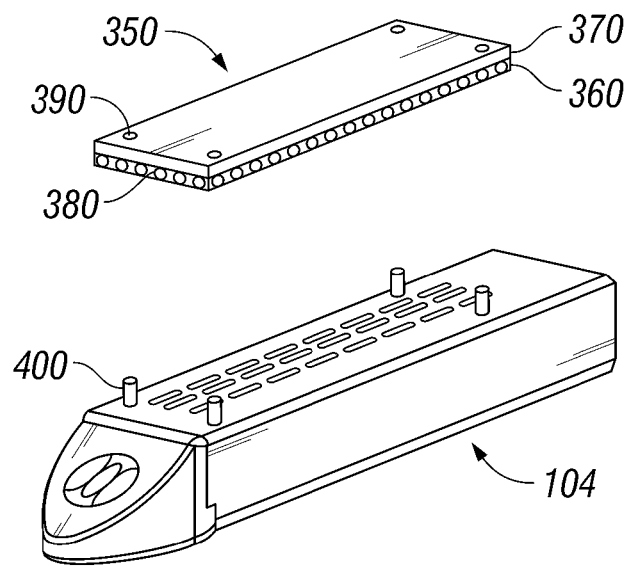
FIG. 4 is a perspective view of a staple cartridge that includes a multilayer buttress releasably attached thereto.

Turning now to FIG. 4, one embodiment is shown in which multilayer buttress 350 includes at least one hole 390 which is shaped and designed to frictionally fit onto at least one pin 400 located on staple cartridge 104 and/or staple anvil 204. Hole 390 and pin 400 are designed to releasably attach multilayer buttress 350 to staple cartridge 104 and/or staple anvil 204 and both can be of any size, shape or dimension.

In some embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medial device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin, lactoferricin B and antimicrobial polysaccharides such as fucans and derivatives may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; antimigraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

EXAMPLE 1

Preparation of Porous Layer

Type I porcine collagen is extracted from pig dermis and rendered soluble through pepsin digestion and purified by saline precipitation.

A 10 g/l solution of the collagen is prepared by dissolving 23 g of damp collagen (12% humidity) in 2070 g of ultrafiltered water, at an ambient temperature below 25° C. It is neutralized using sodium hydroxide to a neutral pH, which leads to precipitation of the collagen.

A porous layer suitable for use in making a multilayer buttress is prepared by poring the suspension onto freeze-dry plates, with 0.5 to 1 g/cm² and freeze-drying, using one cycle lasting about 24 hours.

Optionally, in a variant, the freeze-dried porous layer so produced can be heated to 60° C. for several hours (4 to 15), which provides it with better cohesion and mechanical resistance in certain applications.

Preparation of a Solution of Oxidized Collagen Used to Form a Non-Porous Film

Type I porcine collagen is extracted from pig dermis and rendered soluble through pepsin digestion and purified by saline precipitation.

A 30 g/l solution of oxidized collagen used for this example, is prepared according to patent FR-A-2 715 309.

Dry collagen fibres are used for preference, obtained by precipitation of an acid solution of collagen by adding NaCl, then washing and drying the precipitate obtained using aqueous solutions of acetone in concentrations increasing from 80% to 100%.

A 30 g/l solution of collagen is prepared by dissolving it in 0.01 N HCl. Its volume is 49 liters. Periodic acid is added to it at a final concentration of 8 mM, i.e. 1.83 g/l. Oxidation takes place at an ambient temperature close to 22° C. for 3 hours away from light.

Then an equal volume of a solution of sodium chloride is added to the solution to obtain a final concentration of 41 g/l NaCl.

After waiting for 30 minutes, the precipitate is collected by decantation through a fabric filter, with a porosity close to 100 microns, then washed 4 times with a 41 g/l solution of NaCl in 0.01 N HCl. This produces 19 kg of acid saline precipitate. This washing process eliminates all traces of periodic acid or iodine derivatives during oxidation of the collagen.

Then, several washes in an aqueous solution of 80% acetone are used to concentrate the collagen precipitate and eliminate the salts present.

A final wash in 100% acetone is used to prepare 3.6 kg of a very dense acetone precipitate of acid, oxidized, non-reticulated collagen, with no trace of undesirable chemical products.

The acetone paste is diluted with apyrogenic distilled water at 40° C., to obtain a 3% concentration of collagen, for a volume of 44 liters. The collagen suspension of a volume of 44 liters is heated for 30 minutes at 50° C., then filtered under sterile conditions through a membrane of 0.45 micron porosity in a drying oven at 40° C.

As soon as this solution is homogeneous and at 35° C., a sterile concentrated solution of PEG 4000 (polyethylene glycol with a molecular weight of 4000 Daltons) and glycerine is added to it to produce a final concentration of 0.9% PEG, 0.54% glycerine and 2.7% oxidized collagen.

As soon as these additions have been made, the pH of the solution is adjusted to 7.0 by adding a concentrated solution of sodium hydroxide.

Preparation of a Multilayer Buttress Material

The collagen solution destined to form the non-porous layer, as described in above, is poured in a thin layer on a flat hydrophobic support such as PVC or polystyrene, at an ambient temperature close to 22° C. A continuous pocket, or channel, or a plurality of longitudinally spaced pockets, or channels, are machined into the surface of the hydrophobic support. The pockets, or channels, in the support correspond to slots or openings in the anvil and/or staple cartridge. The number, dimension and spacial relationship of the pockets, or channels, are determined so as to provide a molded buttress which in turn provides a releasable pressure fit with the slots or openings provided in the anvil or staple cartridge when placed in cooperation therewith.

The porous layer, prepared as described above, is applied uniformly to the solution of heated collagen, 5 to 20 minutes after it was poured onto the support. This waiting time is the collagen solution gelling time, required for application of the porous layer, to prevent it dissolving or becoming partially hydrated in the liquid collagen.

Penetration of the porous layer into the gelled collagen solution can be less than 0.5 mm.

The buttress material is then dehydrated in a jet of sterile air, at ambient temperature, which leads to evaporation in about 18 hours.

The multilayer buttress material obtained is easy to remove from the support and can be cut to the dimensions required for the application concerned, without weakening it.

The multilayer buttress material is then put into an airtight double polyethylene bag.

The unit is sterilized by gamma irradiation or electron beam (beta) irradiation at a dose of between 25 and 35 KGy.

The material is stable at ambient temperature.

EXAMPLE 2

Preparation of a Multilayer Buttress Material

The collagen solution destined to form the non-porous layer, as described above in EXAMPLE 1, is poured in a thin layer equal to about 0.106 g/cm$^2$ on a flat hydrophobic support such as PVC or polystyrene, at an ambient temperature close to 22° C. Several protrusions are machined onto the surface of the mold. The protrusions on the mold correspond to the pins located on the anvil and/or staple cartridge. The number, dimension and spacial relationship of the protrusions, are determined so as to provide a molded buttress which in turn provides a releasable pressure fit with the pins provided on the anvil or staple cartridge when placed in cooperation therewith.

The remaining collagen solution is diluted with ethyl alcohol and water to produce a final concentration of 1.75% of oxidized collagen.

Using the diluted solution of 1.75% oxidized collagen, a second layer equal to about 0.041 g/cm$^2$ is poured over the first layer, 1 hour or more after the spreading of the first layer.

Immediately, a surgical mesh reinforcement member is applied on the second layer of the diluted oxidized collagen. The reinforcement member is a knitted isoelastic, multifilament polyglycolic acid mesh which may be completely encapsulated by the second layer of oxidized collagen.

After 1 hour or more, the porous layer, prepared as described above in EXAMPLE 1, is applied to the mesh.

The multilayer, reinforced buttress material is dried in a drying cabinet at about 20° C. and about 40% humidity with a horizontal air flow velocity of 1.2 m$^2$/s. The air is blown from the right side of the cabinet to the left side of the cabinet and the incoming air is 0.2 μm filtered and adjusted to 40% humidity. The duration of the drying cycle is between 12 and 24 hours.

EXAMPLE 3

Preparation of a Multilayer Buttress Material

The collagen solution destined to form the non-porous, as described above in EXAMPLE 1, is poured in a thin layer equal to about 0.106 g/cm$^2$ on a flat hydrophobic support such as PVC or polystyrene, at an ambient temperature close to 22° C.

The remaining collagen solution is diluted with ethyl alcohol and water to produce a final concentration of 1.75% of oxidized collagen.

Using the diluted solution of 1.75% oxidized collagen, a second layer equal to about 0.041 g/cm$^2$ is poured over the first layer, 1 hour or more after the spreading of the first layer.

Immediately, a surgical mesh reinforcement member, is applied on the second layer of the diluted oxidized collagen. The reinforcement member is a knitted isoelastic, multifilament polyglycolic acid mesh which may be positioned on top of the second layer of oxidized collagen.

After 1 hour or more, the porous layer, prepared as described above in EXAMPLE 1, is applied to the mesh.

The multilayer, reinforced buttress material is dried in a drying cabinet at about 20° C. and about 40% humidity with a horizontal air flow velocity of 1.2 m$^2$/s. The air is blown from the right side of the cabinet to the left side of the cabinet and the incoming air is 0.2 μm filtered and adjusted to 40% humidity. The duration of the drying cycle is between 12 and 24 hours.

The multilayer buttress of EXAMPLES 1-3 are applied to the staple cartridge and/or anvil of a surgical stapler, with the non-porous side in contact with the surface of the cartridge and/or anvil. The edges of a wound are approximated between the staple cartridge and the staple anvil of the stapling apparatus. By firing the stapling apparatus staples are forced out of the staple cartridge and through both the multilayer buttress and, the tissue. The staples are formed by contact with the staple anvil. Once stapled in place the porous layer advantageously reduces bleeding, assists in sealing the wound and allowing tissue ingrowth, if desired, while the non-porous layer provides support for the porous layer and may assist in preventing the formation of adhesions. When present, as in EXAMPLES 2 and 3, the reinforcement member provides additional support to the multilayer buttress and assist in preventing tears during stapling.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A surgical stapling apparatus comprising:
   a staple cartridge containing at least one staple and including a staple ejecting surface having an opening through which the at least one staple is ejected;
   an anvil having a staple forming surface, wherein one of the staple ejecting surface of the staple cartridge or the staple forming surface of the anvil includes a plurality of pins, each pin of the plurality of pins extending along an axis transverse to the staple ejecting surface or the staple forming surface, and laterally spaced inwardly of outer side edges of the staple ejecting surface or the staple forming surface; and
   a buttress positioned on the staple cartridge or the anvil, the buttress having at least one bioactive agent, and including a plurality of holes extending therethrough, the buttress releasably attached to the staple cartridge or the anvil by frictional engagement of each hole of the plurality of holes of the buttress with a pin of the plurality of pins of the staple cartridge or the anvil.

2. The surgical stapling apparatus according to claim 1, wherein the buttress has more than one layer.

3. The surgical stapling apparatus according to claim 1, wherein the buttress has a porous layer including a plurality of pores and a non-porous layer.

4. The surgical stapling apparatus according to claim 3, wherein the non-porous layer is an adhesion barrier.

5. The surgical stapling apparatus according to claim 3, wherein the non-porous layer is a film.

6. The surgical stapling apparatus according to claim 3, wherein the non-porous layer is in contact with the staple cartridge or the anvil to which the buttress is releasably attached.

7. The surgical stapling apparatus according to claim 3, wherein the porous layer is a fibrous structure.

8. The surgical stapling apparatus according to claim 3, wherein the porous layer is partially disposed within the non-porous layer.

9. The surgical stapling apparatus according to claim 3, wherein at least one of the porous layer or the non-porous layer is formed from a non-bioabsorbable material.

10. The surgical stapling apparatus according to claim 2, wherein the buttress has at least one reinforcement member.

11. The surgical stapling apparatus according to claim 10, wherein the at least one reinforcement member is a mesh.

12. The surgical stapling apparatus according to claim 10, wherein the at least one reinforcement member is selected from the group consisting of monofilaments, multifilament braids, chopped fibers, and combinations thereof.

13. The surgical stapling apparatus according to claim 10, wherein the at least one reinforcement member includes a first reinforcement member oriented in a first direction and a second reinforcement member oriented in a second direction.

14. The surgical stapling apparatus according to claim 13, wherein the first and second reinforcement members are disposed in different layers of the buttress.

15. The surgical stapling apparatus according to claim 1, wherein the bioactive agent is selected from the group consisting of anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, enzymes, and combinations thereof.

16. The surgical stapling apparatus according to claim 1, wherein the bioactive agent is selected from the group consisting of anti-tumor agents and tumor suppressors.

17. The surgical stapling apparatus according to claim 1, wherein the buttress includes material derived from animal collagen.

18. The surgical stapling apparatus according to claim 1, wherein the buttress includes a gelled collagen solution applied in a layer and dried.

19. The surgical stapling apparatus according to claim 1, wherein the buttress includes oxidized collagen.

20. The surgical stapling apparatus according to claim 1, wherein the plurality of holes of the buttress are disposed in corners of the buttress.

21. The surgical stapling apparatus according to claim 1, further comprising at least one of an adhesive, a sealant, or a glue disposed between the buttress and the staple cartridge or the anvil to which the buttress is releasably attached.

22. The surgical stapling apparatus according to claim 1, wherein the buttress defines outer side edges that are coterminous with the outer side edges of the staple ejecting surface or the staple forming surface when the buttress is disposed thereon.

23. A surgical stapling apparatus comprising:
a staple cartridge containing at least one staple and including a staple ejecting surface having an opening through which the at least one staple is ejected;
an anvil having a staple forming surface, wherein one of the staple ejecting surface of the staple cartridge or the staple forming surface of the anvil includes a plurality of pins extending transversely therefrom, each pin of the plurality of pins laterally spaced inwardly of an outer perimeter of the staple ejecting surface or the staple forming surface, and including a first end directly coupled to the staple ejecting surface or the staple forming surface, and a free end longitudinally aligned with the first end; and
a buttress positioned on the staple cartridge or the anvil, the buttress having a plurality of holes extending therethrough, the buttress releasably attached to the staple cartridge or the anvil by frictional engagement of the plurality of holes of the buttress with the plurality of pins of the staple cartridge or the anvil.

* * * * *